United States Patent

Arita et al.

[11] Patent Number: 4,990,625
[45] Date of Patent: Feb. 5, 1991

[54] PROCESS FOR SYNTHESIS OF N,N-DISUBSTITUTED HYDRAZONE

[75] Inventors: Tetsuo Arita, Shiki; Minoru Mabuchi, Tokyo; Shoji Umehara, Fuchu; Kiyoshi Sakai, Mitaka, all of Japan

[73] Assignee: Canon Kabushiki Kaisha, Tokyo, Japan

[21] Appl. No.: 445,930

[22] Filed: Dec. 5, 1989

Related U.S. Application Data

[63] Continuation of Ser. No. 110,569, Oct. 15, 1987, abandoned, which is a continuation of Ser. No. 797,791, Nov. 14, 1985, abandoned, which is a continuation of Ser. No. 525,175, Aug. 22, 1983, abandoned.

[30] Foreign Application Priority Data

Aug. 31, 1982 [JP] Japan ............................ 57-150023

[51] Int. Cl.$^5$ .................. C07C 249/16; C07D 209/82
[52] U.S. Cl. ..................................... 548/444; 544/102; 548/503; 548/561; 564/112; 564/251
[58] Field of Search ................ 544/102; 548/444, 503, 548/561; 564/112, 251

[56] References Cited

U.S. PATENT DOCUMENTS

| 2,754,326 | 7/1956 | Bradley | 564/112 |
| 2,945,062 | 7/1960 | Hinman | 564/112 |
| 3,359,316 | 12/1947 | Biel | 564/251 |
| 4,332,948 | 6/1982 | Sakai et al. | 564/251 |

FOREIGN PATENT DOCUMENTS 58-65261 4/1983 Japan .

Primary Examiner—Robert W. Ramsuer
Attorney, Agent, or Firm—Fitzpatrick, Cella, Harper & Scinto

[57] ABSTRACT

A process for synthesizing an N,N-disubstituted hydrazone comprises carrying out nitrozation by adding an aqueous solution of sodium nitrite to a solution having one part by weight of an N,N-disubstituted amine dissolved in 3 to 30 parts by weight of an organic acid, then reducing the nitrozated product to an N,N-disubstituted hydrazine by adding a reducing agent to the mixture containing the nitrozated product, and thereafter adding to the mixture containing the N,N-disubstituted hydrazine a carbonyl compound of the formula:

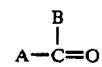

wherein A represents an aromatic hydrocarbon group or an aromatic heterocyclic group which may have a substituent, B represents a hydrogen atom, an alkyl group, an aryl group or an aromatic heterocyclic group, which may have a substituent, thereby performing condensation of the N,N-disubstituted hydrazine with the carbonyl compound.

12 Claims, No Drawings

PROCESS FOR SYNTHESIS OF N,N-DISUBSTITUTED HYDRAZONE

This application is a continuation of application Ser. No. 110,569 filed Oct. 15, 1987, now abandoned, which, in turn is a continuation of Ser. No. 797,791, filed Nov. 14, 1985, now abandoned, which, in turn is a continuation of Ser. No. 525,175, filed Aug. 22, 1983 now abandoned.

BACKGROUND OF THE INVENTION

1. Field of the Invention

This invention relates to a hydrazone compound which is useful as a photoconductive substance to be used in an electrophotographic photosensitive member.

2. Description of the Prior Art

Hydrazone compounds are known to be useful as photoconductive substances to be used in electrophotographic photosensitive members, and application thereof for electrophotographic photosensitive member and also processes for production thereof are disclosed in U.S. Pat. Nos. 4,150,987 and 4,278,747 as well as Japanese Laid-open patent application Nos. 52,064/1980, 81,552/1981 and 81,559/1981.

According to a process of the prior art, a hydrazone compound can be obtained by reducing a nitroso compound to be converted once to a hydrazine compound, which is then isolated and allowed to undergo condensation reaction with a carbonyl compound in a solvent. As the solvent, alcohols such as methanol, ethanol, etc and acetic acid are frequently used.

On the other hand, the aforesaid nitroso compound can be obtained by adding an aqueous solution of sodium nitrite dropwise into an aqueous solution of a hydrochloride of an amine compound. When carrying out the condensation reaction of a hydrazine compound obtained by reduction of this nitroso compound with a carbonyl compound, because this condensation reaction is a reaction which dislikes the presence of water, the hydrazine compound is once isolated and then allowed to undergo the condensation reaction with a carbonyl compound in the absence of water to synthesize a hydrazone compound.

However, most of hydrazine compounds are very unstable to be readily oxidized. When a hydrazine compound formed by reduction of a nitroso compound is once isolated, it is not possible in some cases to derive a hydrazone compound from the hydrazine compound, or the yield is considerably lowered. Moreover, it is difficult to carry out in the same solvent system the reactions

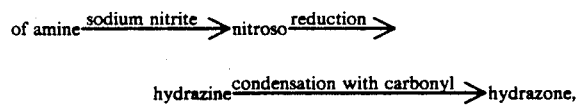

whereby the production efficiency was worsened.

As the method known in the art for synthesizing a hydrazone in the same solvent system, in place of making sodium nitrite used during formation of a nitrosated product into an aqueous solution, anhydrous sodium nitrite powders are used and anhydrous acetic acid is used as the reaction solvent, and a carbonyl compound is added to the resultant liquid reaction mixture containing the nitrosated compound to carry out the condensation reaction.

This reaction, while it has the advantage of carrying out the reactions of amine→nitroso→hydrazine→hydrozone in the same solvent system, involves the drawbacks that nitrosation can difficultly be accomplished completely in the nitrosation reaction, and moreover that sodium nitrite not contributed to the reaction in the nitrosation step will remain in the reaction liquid system, which decomposes the hydrazine compound formed in the hydrazination step by reduction, thereby ultimately lowering markedly the synthesis yield of hydrazone.

SUMMARY OF THE INVENTION

An object of the present invention is to provide a novel process for producing a hydrazone compound and further to provide a process capable of producing a hydrazone compound at high yield.

According to the present invention, there is provided a process for synthesizing an N,N-disubstituted hydrazone which comprises carrying out nitrosation by adding an aqueous solution of sodium nitrite to a solution having one part by weight of an N,N-disubstituted amine dissolved in 3 to 30 parts by weight of an organic acid, then reducing the nitrosated product to an N,N-disubstituted hydrazine by adding a reducing agent to the mixture containing the nitrosated product, and thereafter adding to the mixture containing the N,N-disubstituted hydrazine a carbonyl compound of the formula:

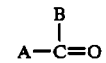

wherein A represents an aromatic hydrocarbon group or an aromatic heterocyclic group which may have a substituent, and B represents a hydrogen atom, an alkyl group, an aryl group or an aromatic heterocyclic group which may have a substituent, thereby performing condensation of N,N-disubstituted hydrazine with the carbonyl compound.

DETAILED DESCRIPTION OF THE PREFERRED EMBODIMENTS

The synthesis process according to the present invention is capable of carrying out the reactions of amine→nitroso=hydrazine→hydrazone in the same solvent system. Particularly, the specific feature in the process of the present invention resides in using as the reaction solvent to be used in the nitrosation step 3 to 30 parts by weight of an organic acid per one part by weight of amine, whereby the condensation reaction can be carried out at high yield in spite of the presence of water in the condensation reaction system. Accordingly, in the process of the present invention, it is not necessary to isolate once the hydrazine compound, and also the reactions can be conducted continuously in the same solvent system to synthesize hydrazone at high yield. That is, according to the synthesis process of the present invention as specified above, an N,N-disubstituted hydrazone can be produced at high yield. The hydrazone compound prepared according to the process of the present invention may include, for example,
p-dimethylaminobenzaldehyde-N-phenyl-N-α-naphthylhydrazone;

p-diethylaminobenzaldehyde-N-phenyl-N-α-naphthlhydrazone;
p-dibenzylaminobenzaldehyde-N-phenyl-N-α-naphthylhydrazone;
p-dimethylaminobenzaldehyde-N-phenyl-N-β-naphthylhydrazone;
p-diethylaminobenzaldehyde-N-phenyl-N-β-naphthylhydrazone;
p-dibenzylaminobenzaldehyde-N-phenyl-N-β-naphthylhydrazone;
p-diethylaminobenzaldehyde-N,N-diphenylhydrazone;
p-dipropylaminobenzaldehyde-N,N-diphenylhydrazone;
p-diethylamino-o-chlorobenzaldehyde-N,N-diphenylhydrazone;
p-diethylaminobenzaldehyde-N-phenyl-N-methylhydrazone;
p-diethylaminobenzaldehyde-N-phenyl-N-benzylhydrazone;
N-methyl-N-phenylhydrazino-3-methylidene-9-ethylcarbazole;
N,N-diphenylhydrazino-3-methylidene-9-ethylcarbazole;
N,N-diphenylhydrazino-3-methylidene-10-ethylphenothiazine;
N,N-diphenylhydrazino-3-methylidene-10-ethylphenoxazine; and
p-pyrrolidinylbenzaldehyde-N,N-diphenylhydrazone.

These hydrazone compounds are useful particularly as a charge transporting substance in the field of electrophotographic photosensitive members. Such a kind of electrophotographic photosensitive member is disclosed in U.S. patent application Ser. No. 325,838, filed on Nov. 30, 1981, now U.S. Pat. No. 4,423,129.

The process of the present invention is explained with respect to the case in which N-phenyl-N-α- or β-naphthylamine is used as an N,N-disubstituted amine which is the starting material of the process.

In the present invention, nitrosation of N-phenyl-N-α- or β-naphthylamine is effected by carrying out the reaction in a homogeneous system in which N-phenyl-N-α- or β-naphthylamine is dissolved in an organic acid such as formic acid, acetic acid or propionic acid, and an aqueous solution of sodium nitrite is added thereto. Preferably, acetic acid is used as the organic acid. For example, the amount of acetic acid to dissolve N-phenyl-N-α- or β-naphthylamine may be 3 to 8 parts by weight, preferably 4 to 7 parts by weight per one part by weight of N-phenyl-N-α-naphthylamine and may be 10 - 30 parts by weight, preferably 12 to 28 parts by weight per one part of N-phenyl-N-β-naphthylamine. The reason why acetic acid is used in an amount within such a range is that, if the amount of acetic acid is too small, precipitation of N-phenyl-N-α- or β-naphthylamine occurs by the influence of water at the time of dropwise addition of an aqueous sodium nitrite solution, whereby the reaction system becomes heterogeneous so that a nitrosated product cannot be obtained at high yield. On the other hand, if the amount of acetic acid is too much, there is no problem in solubility, but during filtration after the subsequent step of reduction, filtration time becomes elongated, whereby N-phenyl-N-α- or β-naphthylhydrazine is oxidized to be a cause in lowering of the yield of the hydrazone compound, and further in increase of the cost.

Next, an aqueous sodium nitrite solution is added dropwise at 30° to 50° C. in the nitrosation step, and the aqueous sodium nitrite solution used has a concentration of 45 to 30% by weight, preferably 41 to 35% by weight. At a higher concentration than said range, sodium nitrite may be precipitated to make the reaction system heterogeneous, while at a lower concentration, acetic acid as the reaction solvent is required to be used in a large amount.

As the next step, N-phenyl N-α- or β-naphthylhydrazine is obtained by adding a reducing agent to the above solution containing a nitroso compound, while controlling the temperature at 10° to 40° C., preferably 15° to 30° C. thereby effecting reduction of said compound. The reason why the reduction is practiced at 10° to 40° C. is for the purpose of prevention of oxidation of the resulting hydrazine compound, and further for the purpose of safety of operations and stability of the production. As the reducing agent, there may be employed metal powders such as of magnesium, aluminum, zinc, iron, etc. When the aforesaid reduction is carried out at a temperature lower than 10° C., the reaction begins after the reducing agent has accumulated to some extent in a reaction system, whereby the liquid temperature is abruptly elevated by the reaction heat, and the temperature can difficultly be controlled until the liquid temperature may exceed 40° C. to worsen the yield. If it is carried out at a temperature higher than 40° C., oxidation of the hydrazine compound formed is accelerated to lower markedly the yield to a great disadvantage. After the reduction, the residual reducing agent is removed by filtration to obtain a solution containing N-phenyl-N-α- or β-naphthylhydrazine. This filtration is required to be conducted rapidly in order to prevent oxidation of the hydrazine compound formed.

The hydrazone compound which is the end product of the present invention can be produced by adding dropwise a solution of a carbonyl compound represented by the formula:

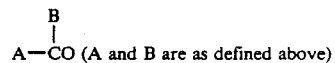

dissolved in a solvent such as acetic acid, methanol, ethanol, 1,4-dioxane, tetrahydrofuran or N,N-dimethylformamide, etc. at a temperature of 35° C. or lower to the solution containing N-phenyl-N-α- or β-naphthylhydrazine and effecting condensation reaction.

The condensation may be conducted at 10° C.–35° C,, preferably 10° C.–25° C., for the purpose of preventing oxidation of N-phenyl-N-α- or β-naphthylhydrazine. This compound is more readily oxidizable under the state where no reducing agent is co-present, and therefore it is not desirable to carry out the reaction at higher than 35° C.

The carbonyl compounds to be used in the present invention is represented by the formula:

wherein A is an aromatic hydrocarbon group such as phenyl, naphthyl, anthryl an the like or an aromatic heterocyclic group such as carbazolyl, phenothiazinyl, phenoxazinyl, indolyl and the like, which may have a substituent, and B is a hydrogen atom, an alkyl group such as methyl, ethyl, propyl and the like, an aryl group such as phenyl and the like or an aromatic heterocyclic group such as carbazolyl, imidazolyl, thiazolyl and the like, which may have a substituent. The substituent for each group included in A and B may be, for example, an alkyl group such as methyl, ethyl, propyl, butyl, amyl, hexyl and the like, an alkoxy group such as methoxy, ethoxy, propoxy, butoxy and the like, a halogen such as chloro, bromo and the like, a substituted amino group such as dimethylamino, diethylamino, dipropylamino, dibutylamino, dibenzylamino and the like, a cyclic amino group such as pyrrolidinyl, morpholino and the like.

Specific compounds are exemplified below:

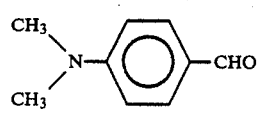
(1)

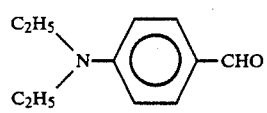
(2)

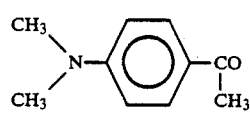
(3)

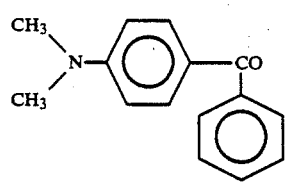
(4)

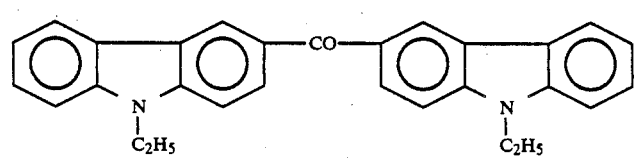
(5)

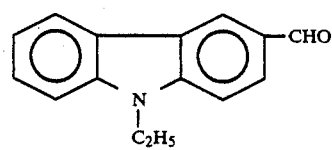
(6)

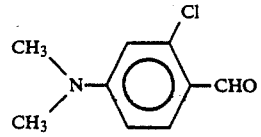
(7)

Also, other than N-phenyl-N-α- or -β-naphthylamine employed in the nitrosation step as described above, it is possible to use, for example, N,N-diphenylamine, N-methyl-N-phenylamine, N-phenyl-N-α-naphthylamine, N-phenyl-N-β-naphthylamine, N,N-di-α-naphthylamine, N-α-naphthyl-N-β-naphthylamine, N-phenyl-N-benzylamine, N-p-methoxyphenyl-N-benzylamine, N-phenyl-N-p-methoxybenzylamine, N-methyl-N-p-methoxyphenylamine, N-ethyl-N-phenylamine and the like.

The reactions in the process of the present invention may be shown below:

N,N-Disubstituted amine of the formula:

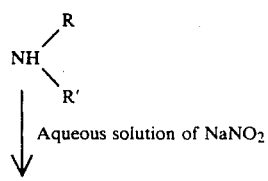

Nitroso compound of the formula:

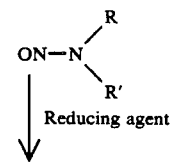

N,N-Disubstituted hydrazine of the formula:

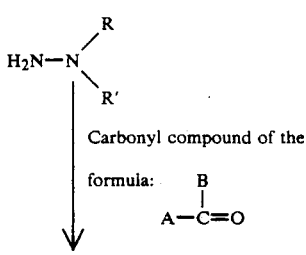

Carbonyl compound of the formula: 
$$A-\underset{\underset{B}{|}}{C}=O$$

N,N-Disubstituted hydrazone of the formula:

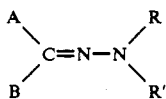

In the formulas, A and B are as defined above, and R and R' are alkyl group such as, methyl, ethyl and the like; aryl group which may have a substituent, such as phenyl, α-naphthyl, β-naphthyl, p-methoxyphenyl and the like; or aralkyl group which may have a substituent, such as benzyl, p-methoxylbenzyl and the like.

The present invention is further illustrated by referring to the following Examples, in which all parts are by weight.

EXAMPLE 1

Preparation of the compound of the structural formula:

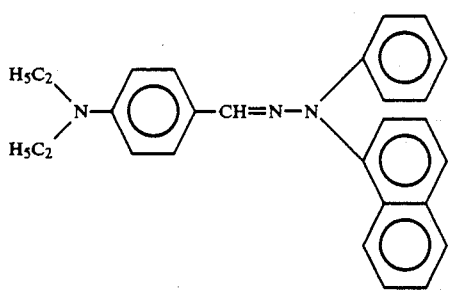

Nitrosation was carried out by adding dropwise an aqueous solution of 7 parts of sodium nitrite dissolved in 10 parts of water into a solution of 10 parts of N-phenyl-N-α-naphthylamine dissolved in 54 parts of acetic acid at 35° C. During this reaction, no precipitation of N-phenyl-N-α-naphthylamine was recognized.

Then, to the solution containing the nitrosated product, 9 parts of zinc powders were added to effect reduction, addition being commenced from 19° C. and controlled so that the temperature does not exceed 25° C. After the reduction, the reaction mixture was subjected immediately to filtration.

Subsequently, to the filtrate was added dropwise a solution of 7.3 parts of 4-N,N-diethylaminobenzaldehyde (Exemplary compound (2) shown above) dissolved in 8 parts of methanol at 20° C. and the reaction was carried out at the same temperature for one hour.

As the next step, this reaction mixture was poured into water to obtain yellow precipitates. The precipitates were filtered, washed with water and dried. Then, recrystallization from methyl ethyl ketone gave 11.1 parts (yield based on amine: 61.9 %) of yellow crystals melting at 143.5° to 144.5° C.

Elemental analysis: Calcd. for $C_{27}H_{27}N_3$: C, 82.39%; H, 6.93%; N, 10.68%, Found: C, 82.36%, H, 6.94%;, N, 10.70%.

COMPARATIVE EXAMPLE 1

(Synthesis of the same hydrazone compound as in Example 1)

Nitrosation was carried out by adding dropwise an aqueous solution of 7 parts of sodium nitrite in 10 parts of water into a solution of 20 parts of N-phenyl-N-α-naphthylamine dissolved in 35 parts of acetic acid at 35° C. However, particles of N-phenyl-N-α-naphthylamine were recognized, and when the hydrazone compound was obtained following the same procedure as in Example 1, there were obtained 6.8 parts of the product, which was 32.0% in terms of the yield based on amine.

The values of elemental analysis were found to be the same as in Example 1.

EXAMPLE 2

Preparation of a hydrazone compound having the following formula:

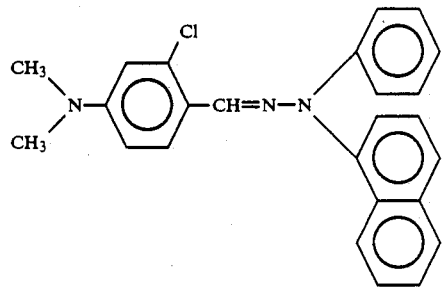

According to the same procedure as in Example 1, there was prepared a solution of N-phenyl-N-α-naphthylhydrazine. Then, to this solution was added dropwise a solution of 7.6 parts of 2-chloro-4-N,N-dimethylaminobenzaldehyde (Exemplary compound (7) shown above) dissolved in 10 parts of methanol at 23° C., and the reaction was carried out at the same temperature for 2 hours. The resultant reaction mixture was poured into water to obtain yellow precipitates. The precipitates were filtered, washed with water and dried, followed by recrystallization from acetone, to obtain 10.5 parts (yield based on amine: 57.8 %) of yellow crystals melting at 140° to 141° C.

Elemental analysis: Calcd. for $C_{25}H_{22}N_3Cl$: C, 75.09%; H, 5.51%, N, 10.51%; Cl, 8.89%, Found: C, 75.11%, H, 5.50%; N, 10.52%; Cl, 8.87%.

EXAMPLE 3

Preparation of a hydrazone compound having the following formula:

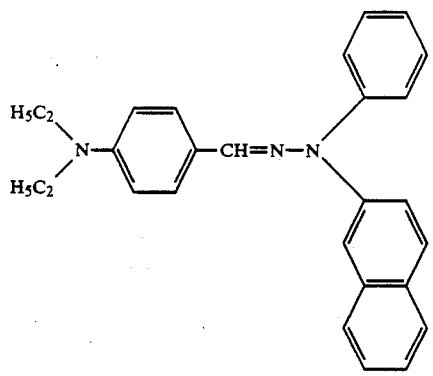

Nitrosation, reduction and condensation were carried out according to the same procedures as in Example 1, except that 10 parts of N-phenyl-N-β-naphthylamine were dissolved in 120 parts of acetic acid, and the product obtained was recrystallized from methyl ethyl ketone to obtain 10.7 parts (yield based on amine: 59.8%) of yellow crystals melting at 128.5° to 129.5° C.

Elemental analysis: Calcd. for $C_{27}H_{27}N_3$: C, 82.39%, H, 6.93%, N, 10.68%, Found: C: 82.39%, H, 6.95%; N, 10.67%.

COMPARATIVE EXAMPLE 3

(Synthesis of the same hydrazone compound as in Example 3)

Nitrosation was carried out by adding 87 g (1.26 mole) of sodium nitrite into a solution of 250 g (1.14 mole) of N-β-naphthylaniline dissolved in 5 liters of 35% aqueous hydrochloric acid. The reaction mixture was cooled to 10° C., and 87.5 g (1.14 mole) of zinc powders were added portionwise. Then, the mixture was filtered and water was injected into the filtered product to isolate a hydrazine compound. As the next step, this hydrazine compound was dissolved in one liter of ethanol, and 202 g (1.14 mole) of 4-N,N-diethylaminobenzaldehyde was added to the solution, followed by cooling to 10° C. Then, 250 g (3.82 mole) of zinc was added so that the temperature should not exceed 20° C. Further, this reaction mixture was filtered, and the filtrate poured into water to obtain yellow precipitates. Recrystallization of the yellow precipitates from methyl ethyl ketone gave 73 g of yellow crystals (yield based on amine: 16.3%) melting at 127.0° to 128.0°C. The values of elemental analysis were identical with those of Example 3.

COMPARATIVE EXAMPLE 3

(Synthesis of the same compound as in Example 3)

A nitroso compound represented by the structural formula:

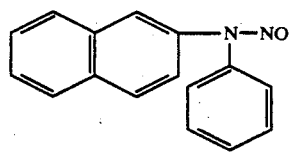

(35 g (0.14 mole)) was dissolved in 230 ml of acetic acid and cooled to 10°C., and 87.5 g (1.14 mole) of zinc powders were added portionwise into the solution. Subsequently, this mixture was filtered and poured into water to isolate a hydrazone compound. Then, this hydrazine compound was dissolved in 110 ml of ethanol, and 24.81 g (0.14 mole) of 4,-N,N-diethylaminobenzaldehyde was added to the solution, followed by stirring for 30 minutes. The resultant reaction mixture was poured into water to obtain yellow crystals. Recrystallization of the crystals from methyl ethyl ketone gave 10.23 g (yield: 18.8%) of yellow crystals melting at 120.0 to 121.5° C. The values of elemental analysis were the same as in Example 3.

COMPARATIVE EXAMPLE 4

(Synthesis of the same compound as in Example 3)

Nitrosation was carried out by adding 87 g (1.26 mole) of sodium nirite powders into a solution of 250 g (1.14 mole) of N-β-naphthylaniline dissolved in 5 liters of 35% aqueous hydrochloric acid. To this mixture was added 202 g (1.14 mole) of 4-N,N-diethylaminobenzaldehyde, followed by cooling to 10° C., and 250 g (3.82 mole) of zinc was added to this mixture so that the temperature should not exceed 20° C. Then, the mixture was filter-d and the filtrate was poured into water, but not desired precipitate was obtained.

EXAMPLE 4

Preparation of a hydrazone compound having the following formula:

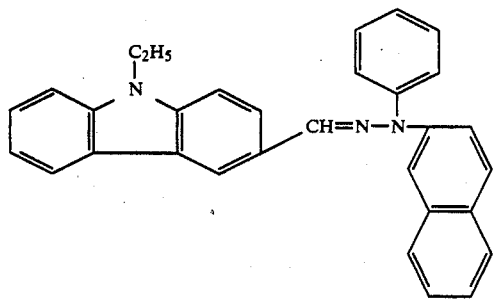

By use of a solution of 10 parts of N-phenyl-N-β-naphthylamine dissolved in 120 parts of acetic acid, following otherwise the same procedures in Example 1, nitrosation and reduction were conducted to obtain a solution of N-phenyl-N-β-naphthylhydrazine. Subsequently, a solution of 9.2 parts of 3-formyl-9-ethylcarbazole (Exemplary compound (6) shown above) dissolved in 35 parts of acetic acid was added dropwise into this solution, and the reaction was carried out at 20° C. for 2 hours. Then, the reaction mixture was poured into water and the yellow precipitates were filtered, washed with water and dried. Recrystallization from methyl cellosolve gave 12.2 parts (yield based on amine: 61.1%) of yellow crystals melting at 149.5° to 150.5° C.

Elemental analysis: Calcd. for $C_{31}H_{25}N_3$: C, 84.74%, H, 5.69%, N, 9.57%, Found: C, 84.72%, H, 5.70%; N, 9.58%.

What we claim is:

1. A continuous process for synthesizing an N,N-disubstituted hydrazone of high purity in high yields comprising:
   (a) adding an aqueous solution of sodium nitrite to a solution having one part by weight of an N,N-disubstituted amine selected from the group consisting of N-phenyl-N-α-naphthylamine and N- phenyl-N-β-naphthylamine dissolved in 3 to 30 parts by weight of an organic acid to form by nitrosation a mixture containing a nitrosated N,N-disubstituted amine product;
(b) adding a reducing agent to said mixture containing said nitrosated product to reduce the nitrosated product to a N,N-disubstituted hydrazine;
(c) conducting step (b) within a temperature range sufficient to provide a controlled reducing rate while preventing substantial oxidation of the N,N-disubstituted hydrazine;
(d) adding a carbonyl compound to the mixture containing the N,N-disubstituted hydrazine to thereby form by condensation the N,N-disubstituted hydrazone; and
(e) conducting step (d) within a temperature range sufficient to prevent substantial oxidation of the N,N-disubstituted hydrazine, wherein said carbonyl compound having the formula

wherein A is a substituted or unsubstituted aromatic hydrocarbon or aromatic heterocyclic group, and B is a hydrogen atom, an alkyl group, an aryl group, or a substituted or unsubstituted aromatic heterocyclic group.

2. A process for synthesizing an N,N-disubstituted hydrazone according to claim 1, wherein A is a substituted aromatic hydrocarbon or aromatic heterocyclic group substituted with a substituent selected from the group consisting of alkyl groups, halogens and substituted amino groups.

3. A process for synthesizing an N,N-disubstituted hydrazone according to claim 1, wherein B is a substituted aromatic heterocyclic group substituted with a substituent selected from the group consisting of alkyl groups, halogens and substituted amino groups.

4. The process for synthesizing an N,N-disubstituted hydrazone according to claim 1, wherein the N,N-disubstituted amine is N-phenyl-N-α-naphthylamine.

5. The process for synthesizing an N,N-disubstituted hydrazone according to claim 1, wherein the N,N-disubstituted amine is N-phenyl-N-β-naphthylamine.

6. The process for synthesizing an N,N-disubstituted hydrazone according to claim 1, wherein the carbonyl compound is selected from the group consisting of the compounds of the formulas:

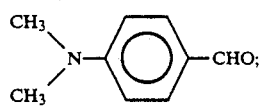 (1)

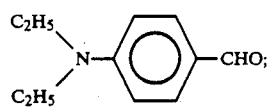 (2)

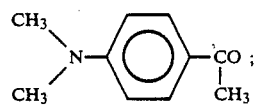 (3)

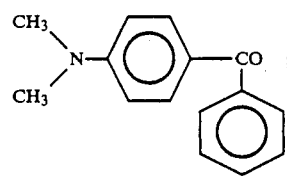 (4)

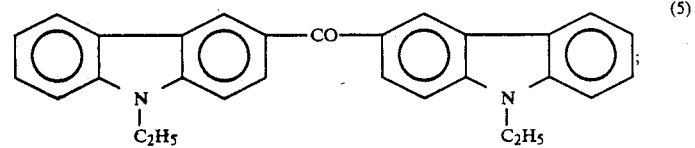 (5)

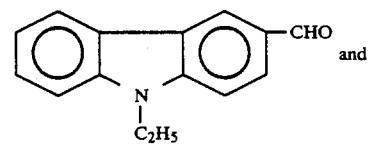 (6) and

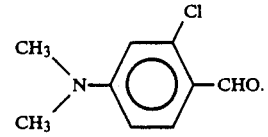 (7)

7. The process for synthesizing an N,N-disubstituted hydrazone according to claim 1, wherein the organic acid is selected from the group consisting of formic acid, acetic acid and propionic acid.

8. The process for synthesizing an N,N-disubstituted hydrazone according to claim 7, wherein the organic acid is acetic acid.

9. The process for synthesizing an N,N-disubstituted hydrazone according to claim 1, wherein the aqueous solution of sodium nitrite contains 30 to 45% by weight of sodium nitrite.

10. The process for synthesizing an N,N-disubstituted hydrazone according to claim 9, wherein the aqueous solution of sodium nitrite contains 35 to 41% by weight of sodium nitrite.

11. The process for synthesizing an N,N-disubstituted hydrazone according to claim 1, wherein the nitrosation reaction is carried out at a temperature of 30° to 50° C.

12. The process for synthesizing an N,N-disubstituted hydrazone according to claim 1, wherein the nitrosated compound is reduced at a temperature of 10° to 40° C.

* * * * *

UNITED STATES PATENT AND TRADEMARK OFFICE
CERTIFICATE OF CORRECTION

PATENT NO. : 4,990,625
DATED : February 5, 1991
INVENTOR(S) : TETSUO ARITA, ET AL.

Page 1 of 2

It is certified that error appears in the above-identified patent and that said Letters Patent is hereby corrected as shown below:

On the title page:
IN [56] REFERENCES CITED

U.S. PATENT DOCUMENTS, "3,359,316 12/1947 Biel" should read --3,359,316 12/1967 Biel--.

IN [57] ABSTRACT

Line 2, "nitrozation" should read --nitrosation--.
Line 6, "nitrozated" should read --nitrosated--.
Line 8, "nitrozated" should read --nitrosated--.

COLUMN 2

Line 49, "nitroso=hydrazine→hydrazone" should read --nitroso→hydrazine→hydrazone--.

COLUMN 5

Line 56, "-62 -naphthyl-" should read --β-naphthyl- --.

COLUMN 9

Line 26, "C: 82.39%," should read --C,82.38%,--.
Line 28, "COMPARATIVE EXAMPLE 3" should read --COMPARATIVE EXAMPLE 2--.

UNITED STATES PATENT AND TRADEMARK OFFICE
CERTIFICATE OF CORRECTION

PATENT NO. : 4,990,625
DATED : February 5, 1991
INVENTOR(S) : TETSUO ARITA, ET AL.

It is certified that error appears in the above-identified patent and that said Letters Patent is hereby corrected as shown below:

COLUMN 10

Line 2, "hydrazone" should read --hydrazine--.
Line 23, "filter-d" should read --filtered--.
Line 24, "not" should read --no--.

Signed and Sealed this

Twenty-second Day of September, 1992

Attest:

DOUGLAS B. COMER

Attesting Officer

Acting Commissioner of Patents and Trademarks